US011802147B2

(12) United States Patent
Bever et al.

(10) Patent No.: US 11,802,147 B2
(45) Date of Patent: Oct. 31, 2023

(54) HIGH AFFINITY MONOCLONAL ANTIBODIES FOR DETECTING AMANITINS

(71) Applicant: The United States of America, as represented by the Secretary of Agriculture, Washington, DC (US)

(72) Inventors: Candace R. Bever, Martinez, CA (US); Larry H. Stanker, Livermore, CA (US); Robert M. Hnasko, Pinole, CA (US); Luisa W. Cheng, San Francisco, CA (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 733 days.

(21) Appl. No.: 16/905,942

(22) Filed: Jun. 19, 2020

(65) Prior Publication Data

US 2021/0002357 A1 Jan. 7, 2021

Related U.S. Application Data

(60) Provisional application No. 62/870,340, filed on Jul. 3, 2019.

(51) Int. Cl.
*C07K 16/14* (2006.01)
*G01N 33/68* (2006.01)

(52) U.S. Cl.
CPC ............ *C07K 16/14* (2013.01); *G01N 33/68* (2013.01); *G01N 2333/37* (2013.01)

(58) Field of Classification Search
None
See application file for complete search history.

(56) References Cited

U.S. PATENT DOCUMENTS

2013/0017561 A1 1/2013 Marr et al.

FOREIGN PATENT DOCUMENTS

WO 2012091465 A2 7/2012

OTHER PUBLICATIONS

He, Kuo et al., Production of a broad-specificity monoclonal antibody and application as a receptor to detection amatoxins in mushroom, Biologicals, 2017, vol. 49, pp. 57-61 abstract; and pp. 59-60.
Falconar, Andrew K.I et al. , IMMUNOaffinity purification of native dimer forms of the flavivirus non-structural glycoprotein, NSI, Journal of Virological Methods, 1990, vol. 30, No. 3, pp. 323-332 pp. 325-326.
Bever, Candace S. et al., A new conjugation method used for the development of an immunoassay for the detection of amanitin, a deadly mushroom toxin, Toxins, 2018, vol. 10, No. 7, Article No. 265 internal pp. 3-7.
Bever, Candace S. et al., A rapid extraction method combined wi th a monoclonal antibody-based immunoassay for the detect ion of amatoxins, Toxins, Dec. 11, 2019 (Publication date), vol. 11, No. 12, Article No. 724 internal pp. 3-9.
International Search Report dated Oct. 15, 2020, (11 pages).

*Primary Examiner* — Ellen J Marcsisin
(74) *Attorney, Agent, or Firm* — John D. Fado; Mark D. McNemar

(57) ABSTRACT

Amatoxins (AMAs) are lethal toxins found in a variety of mushroom species. Detection methods are needed to determine the occurrence of AMAs in mushroom species, often suspected in mushroom poisonings. Provided herein are novel, sensitive monoclonal antibodies (mAbs) detection and purification techniques utilizing the mAbs that show selectivity for α-amanitin (α-AMA), β-amanitin (β-AMA) and γ-amanitin (γ-AMA).

16 Claims, 4 Drawing Sheets

HIGH AFFINITY MONOCLONAL ANTIBODIES FOR DETECTING AMANITINS

CROSS-REFERENCE

The present application claims priority to U.S. Provisional Patent Application Ser. No. 62/870,340 filed Jul. 3, 2019, the content of which is expressly incorporated herein by reference.

BACKGROUND OF THE INVENTION

Field of Invention

The present disclosure provides hybridomas producing monoclonal antibodies that bind to α-amanitin (α-AMA), β-amanitin (β-AMA) and γ-amanitin (γ-AMA). Further provided herein are kits, purification columns, and detection devices utilizing the monoclonal antibodies for detection and differentiation of amatoxins. Techniques for utilizing the antibodies and devices are also provided.

Background

There are thousands of reported mushroom poisonings occurring world-wide each year. The most severe cases are from amatoxin-containing mushrooms. Amatoxin-containing mushrooms include a few species from the genera *Amanita, Galerina*, and *Lepiota*. The principle toxins responsible for the poisonings are the bicyclic octapeptides known as amatoxins, most notably α-amanitin (α-AMA) and β-amanitin (β-AMA), and γ-amanitin (γ-AMA). Amatoxins are potent inhibitors of RNA polymerase II with bioactivity resistant to heat, cold, or acid inactivation. The typical distribution of α-AMA, β-AMA, and γ-AMA in an *Amanita phalloides* mushroom is approximately 43%, 43% and 14%, respectively (Vetter, J., Toxicon, (1998) 36:13-24; Enjalbert, et al, J. Chromatogr., (1992) 598:227-36). A single dried mushroom typically contains around 2 mg/g of amatoxins (Yilmaz, et al, Wilderness Environ. Med., (2015) 26:491-6; Enjalbert et al, C. R. Acad. Sci. III, (1999) 322:855-62; Enjalbert, et al (1992)).

The most common method for the detection of amatoxins extracted from mushrooms is liquid chromatography (LC) coupled with UV detection or mass spectrometry (Garcia et al, Mycologia, (2015) 107:679-687; Sgambelluri et al, Toxins (Basel), (2014) 6:2336-47; Hu et al, J. Sci. Food Agric., (2012) 92:2664-7; Enjalbert, et al (1992)). Although these methods are sensitive and provide a high resolution of individual analytes, they are time-consuming, require expensive laboratory-based instrumentation, and highly trained personnel to interpret the results. In contrast, immunoassays are faster, can be field portable, and require less sophisticated instrumentation. The only commercially available antibody-based assay for amanitin detection for research purposes is the Buhlmann assay (Amanitin ELISA EK-AM1. AG, B. L., Ed. Switzerland, 2013). This assay relies on a polyclonal antibody, which has several drawbacks. For example, once the supply of antibody is depleted, the assay will have to be reevaluated for sensitivity and selectivity using a newly produced polyclonal antibody. Because monoclonal antibodies (mAbs) are produced by a hybridoma cell line derived from a single cell, they overcome this limitation and have little or no batch-to-batch variability. Assays utilizing mAbs thus are more desirable for long-term consistency and can be scaled-up for test kit manufacture. Only a few mAbs to amatoxins have been described, and only one has been used for analytical detection (He et al, Biologicals, (2017) 49:57-61; Faulstich et al, Toxicon, (1988) 26:491-9).

Herein we provide the details of the generation of mAbs utilizing a previously reported immunogen (Bever et al, Toxins, (2018) 10:265), to develop a sensitive and selective amanitin-specific immunoassay for toxin detection from mushrooms. We describe and characterize novel anti-amanitin mAbs and detail their performance in detecting and isolating amatoxins. A sensitive detection assay for amatoxins combined with a rapid and simple toxin extraction method would be a highly useful tool for the determination of amanitin presence in wild mushrooms. The mAbs can also be used to purify one or more amanitins from samples.

SUMMARY OF THE INVENTION

Provided herein are monoclonal antibodies, namely a monoclonal antibody produced by a hybridoma cell line of ATCC deposit accession number PTA-125922 or PTA-125923. In some instances, the antibodies disclosed herein are isolated and purified.

Also provided herein are compositions comprising the monoclonal antibody of claim 1. In some embodiments, the antibodies have a label, such as enzyme labels, radioisotopic labels, non-radioactive isotopic labels, chromogenic labels, fluorescent labels, chemiluminescent labels, and combinations thereof.

Also provided herein are hybridoma cell lines which produce the monoclonal antibodies described herein. In specific embodiments, the cell lines have ATCC deposit accession number PTA-125522 or PTA-125523.

The present disclosure further provides a method for detecting alpha-amanitin, beta-amanitin, or gamma-amanitin in a sample, comprising the steps of: (i) incubating a sample with a monoclonal antibody produced by a hybridoma cell line of ATCC deposit accession number PTA-125922 or PTA-125923; and (ii) detecting an immunological complex of the monoclonal antibody and the alpha-amanitin, beta-amanitin, or gamma-amanitin, where the presence or absence of the immunological complex indicates the presence or absence of the alpha-amanitin, beta-amanitin, or gamma-amanitin in the sample. In some embodiments, the sample is a human sample or an animal sample, such as a urine sample. In other embodiments, the sample is a mushroom extract. In some embodiments, the mushroom extract does not contain an organic solvent. In some embodiments, the method includes the further step of isolating the immunological complex formed between the amanitin and the monoclonal antibody.

The present disclosure also provides a kit for detecting alpha-amanitin, beta-amanitin, or gamma-amanitin in a sample, where the kit has a container comprising a monoclonal antibody produced by a hybridoma cell line of deposit accession number PTA-125922, PTA-125923, or mixtures thereof; and instructions for using the antibody for the purpose of binding to alpha-amanitin, beta-amanitin, or gamma-amanitin to form an immunological complex and detecting the formation of the immunological complex such that presence or absence of immunological complex correlates with presence or absence of alpha-amanitin, beta-amanitin, or gamma-amanitin in said sample. Such a kit can be a lateral flow device.

Also provided herein is a method for purifying an amanitin from a sample, comprising the steps of: (i) incubating a sample comprising the amanitin with a monoclonal antibody produced by a hybridoma cell line of ATCC deposit accession number PTA-125922 or PTA-125923 under conditions where an immunological complex comprising the monoclonal antibody and the amanitin is formed; (ii) isolating the immunological complex from the sample; (iii) decoupling the immunological complex resulting in the release of the amanitin from the monoclonal antibody; and (iv) separating the amanitin from the monoclonal antibody, thereby purifying the amanitin. In one embodiment, the amanitin is alpha-amanitin, beta-amanitin, or gamma-amanitin and the monoclonal antibody is produced by a hybridoma cell line of deposit accession number PTA-125922 (mAb 9G3.2). In another embodiment, the amanitin is alpha-amanitin, or gamma-amanitin and the monoclonal antibody is produced by a hybridoma cell line of deposit accession number PTA-125523 (mAb 9C12.2)

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The novel features of the invention are set forth with particularity in the claims. Features and advantages of the present invention are referred to in the following detailed description, and the accompanying drawings of which:

STATEMENT OF DEPOSIT

Figure 1A:
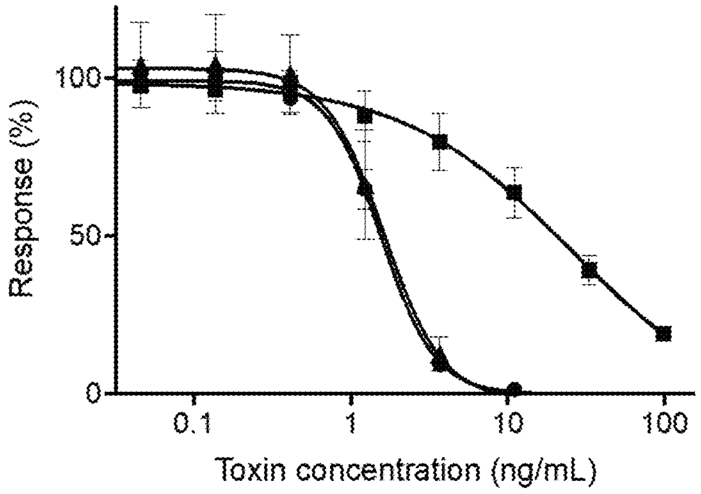
FIG. 1A and FIG. 1B provide standard cELISA inhibition curves for monoclonal antibodies produced by: 1) FIG. 1A—hybridoma PTA-125922 (mAb 9G3.2), and; 2) FIG. 2A hybridoma PTA-125923 (mAb 9C12.2) against toxins α-amanitin (circles), β-amanitin (squares), and γ-amanitin (triangles).

Monoclonal antibodies (mAb) to amatoxins were deposited Jun. 4, 2019 under the terms of the Budapest Treaty with the American Tissue Culture Collection (ATCC) P.O. Box 1549, Manassas, Va., 20108, USA. The “AMA9G3” or “9G3.2” monoclonal antibody is produced by the hybridoma deposited under American Type Culture Collection (ATCC) Accession No. PTA-125922 and recognizes α-AMA, β-AMA, and γ-AMA. The “AMA9C12” or “9C12.2” monoclonal antibody is produced by the hybridoma deposited under American Type Culture Collection (ATCC) Accession No. PTA-125923 and recognizes α-AMA and β-AMA. The deposit was made under the provisions of the “Budapest Treaty on the International Recognition of the Deposit of Microorganisms for the Purposes of Patent Procedure”. All restrictions on the availability to the public of these deposited hybridomas will be irrevocably removed upon issuance of a United States patent based on this application. For the purposes of this invention, any mAb having the identifying characteristics of PTA-125922 and PTA-125923 including subcultures and variants thereof which have the identifying characteristics and activity as described herein are included.

DETAILED DESCRIPTION OF THE INVENTION

Herein are provided the details of the generation of mAbs utilizing a previously reported immunogen (Bever et al, supra), to develop a sensitive and selective amatoxin (α-amanitin, β-amanitin, and γ-amanitin) immunoassay for toxin detection from mushrooms. We describe and characterize novel anti-amatoxin mAbs and detail their performance in detecting and isolating amatoxins. A sensitive detection assay for amatoxins combined with a rapid and simple toxin extraction method would be a highly useful tool for the determination of AMA presence in wild mushrooms.

In some embodiments, the present invention relates to two novel mAbs having specificity for α-amanitin (α-AMA), β-amanitin (β-AMA) and/or γ-amanitin (γ-AMA). Herein is described the development and characterization of novel high-affinity monoclonal antibodies that specifically recognize these toxins as well as methods of using the antibodies to detect the presence of these toxins in samples, such as medical, veterinary and collected mushroom samples. The two described antibodies are independent, but both show specificity for amatoxins as detailed below. For example, it was discovered that one mAb selectively binds α-AMA, β-AMA, and γ-AMA and the other selectively binds to α-AMA and β-amanitin, but not γ-AMA.

Regardless of the method used to detect the amatoxin, extraction is required before identification. Over the years, the extraction procedure has been streamlined from 24 hours (Yilmaz et al, (2015); McKnight et al, Mycologia, (2010) 102:763-5; Enjalbert et al, (1992)) to one hour (Bever et al, supra; He et al, (2017); Garcia et al, (2015); Sgambelluri et al, (2014)). Most of these methods have utilized an extraction solution consisting of methanol, acid, and water prior to mass spectrometry. Development of antibody-based immunoassays, which can be less prone to matrix interferences can utilize simpler water-based extraction methods. Given the high-water solubility of AMAs and their overall abundance in mushroom tissue, we hypothesized that a water-based AMA extraction would be sufficient for immunoassay detection using the highly selective mAbs of the present disclosure.

It is noted that both mAbs described herein can be utilized for detection, isolation, and purification of amatoxins in a variety of settings and in a variety of devices. The mAbs described herein, can be used, for example in human clinical, or animal veterinary, settings to diagnose amanitin poisoning. Additionally, mAbs of the present disclosure can be utilized to detect the presence of amatoxins in a clinical, veterinary or mushroom sample. mAbs disclosed herein can be utilized to purify amatoxins from samples by, for example, affinity purification. Chimeric or humanized antibodies having the amatoxin-binding capability of the disclosed mAbs could also be utilized therapeutically.

Preferred embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby.

Technical and scientific terms used herein have the meanings commonly understood by one of ordinary skill in the art to which the instant invention pertains, unless otherwise defined. Reference is made herein to various materials and methodologies known to those of skill in the art. Standard reference works setting forth the general principles of recombinant DNA technology include Sambrook et al., "Molecular Cloning: A Laboratory Manual", 2d ed., Cold Spring Harbor Laboratory Press, Plainview, N.Y., 1989; Kaufman et al., eds., "Handbook of Molecular and Cellular Methods in Biology and Medicine", CRC Press, Boca Raton, 1995; and McPherson, ed., "Directed Mutagenesis: A Practical Approach", IRL Press, Oxford, 1991. A number of immunoassays used to detect and/or quantitate antigens are well known to those of ordinary skill in the art (see e.g., Harlow and Lane, Antibodies: A Laboratory Manual (Cold Spring Harbor Laboratory, New York 1988) 555-612).

Any suitable materials and/or methods known to those of skill can be utilized in carrying out the instant invention. Materials and/or methods for practicing the instant invention are described. Materials, reagents and the like to which reference is made in the following description and examples are obtainable from commercial sources, unless otherwise noted. This disclosure teaches methods and describes tools for producing monoclonal antibodies recognizing one or more isoforms of amatoxin.

The term "consisting essentially of" excludes additional method (or process) steps or composition components that substantially interfere with the intended activity of the method (or process) or composition, and can be readily determined by those skilled in the art (for example, from a consideration of this specification or practice of the invention disclosed herein). This term may be substituted for inclusive terms such as "comprising" or "including" to more narrowly define any of the disclosed embodiments or combinations/sub-combinations thereof. Furthermore, the exclusive term "consisting of" is also understood to be substitutable for these inclusive terms.

As used in the specification and claims, use of the singular "a", "an", and "the" include plural references unless the context clearly dictates otherwise.

The terms isolated, purified, or biologically pure as used herein, refer to material that is substantially or essentially free from components that normally accompany the referenced material in its native state.

The term "about" is defined as plus or minus ten percent of a recited value. For example, about 1.0 g means 0.9 g to 1.1 g and all values within that range, whether specifically stated or not.

The term "antibody" (Ab) or "monoclonal antibody" (mAb) is known and recognized in the art and as used herein is meant to include intact molecules as well as fragments thereof (such as, for example, Fab and $F(ab')_2$ fragments) which are capable of binding α-amanitin (α-AMA), β-amanitin (β-AMA) and/or γ-amanitin (γ-AMA), including variants thereof.

The term "chimeric" refers to antibodies modified to exhibit a desired biological activity (e.g., within humans or another species of animal such as livestock) having a portion of the heavy and/or light chain identical (i.e., homologous) to corresponding portions in antibodies derived from a particular species (e.g., belonging to a particular antibody class or subclass), while the remainder of the antibody is identical to corresponding sequences in antibodies derived from another species or belonging to another antibody class or subclass as well as fragments of such antibodies. Thus, the present disclosure provides for chimeric versions of the deposited and claimed mAbs.

The terms "detecting an immunological complex", "detecting antibody binding", "quantitating an antigen" or grammatical variations thereof are intended to include discovery of the presence or absence of amatoxin(s) in a sample. The presence or absence of such toxins can be detected using any appropriate methodology, such as an immunoassay. Non-exclusive exemplary immunoassays include antibody capture assays, antigen capture assays, two-antibody sandwich assays, lateral flow immunoassays, and immunoaffinity assays.

The term "effective amount" of a compound or property as provided herein is meant such amount as can perform the function of the compound or property for which an effective amount is expressed. As is pointed out herein, the exact amount required will vary from process to process, depending on recognized variables such as the compounds employed, and various internal and external conditions observed as would be interpreted by one of ordinary skill in the art. Thus, it is not possible to specify an exact "effective amount," though preferred ranges have been provided herein. An appropriate effective amount may be determined, however, by one of ordinary skill in the art using only routine experimentation.

The term "humanized" refers to a chimeric antibody (e.g., chimeric immunoglobulins, immunoglobulin chains, or fragments thereof) containing the amino acid sequence from the antigen-binding site of an antibody molecule of a parent or corresponding non-human mAb grafted onto a human antibody framework to confer desired immunologic properties and function within humans. Humanization of non-human antibodies is known in the art and commonly referred to as complementary determining region (CDR) grafting.

Antibodies and Immunoassays

Specific methods to produce antibodies are provided in the Examples below, but one skilled in the art will recognize that any classical or alternative methods can be used to prepare the antibodies of the invention. For instance, the monoclonal antibodies of the present invention can be prepared using classical cloning and cell fusion techniques. The immunogen (i.e., antigen) of interest is typically administered (e.g. intraperitoneal injection) to wild-type mice or transgenic mice, rats, rabbits, or other animal species which can produce native, humanized, or other desired antibodies. The immunogen can be administered alone or as a fusion protein to induce an immune response with adjuvants known to one of skill in the art including, but not limited to oil-based adjuvants, such as Freunds adjuvant, synthetic adjuvants and aluminum salts. Fusion proteins comprise a peptide against which an immune response is desired coupled to a carrier protein, such as β-galactosidase, glutathione S-transferase, keyhole limpet hemocyanin (KLH), and bovine serum albumin, to name a few. In these cases, the peptides serve as haptens with the carrier proteins. After the animal is boosted, for example, three or four times, the spleen is removed and splenocytes are extracted and fused with myeloma cells using the well-known processes of Kohler and Milstein (Nature 256: 495-497 (1975)) and Harlow and Lane (Antibodies: A Laboratory Manual (Cold Spring Harbor Laboratory, New York 1988)). The resulting hybrid cells are then cloned in the conventional manner (e.g. using limiting dilution), screened and the resulting positive clones, which produce the desired monoclonal antibodies, are cultured.

Using the mAbs of the instant disclosure, rapid detection of amatoxins is possible. In embodiments, the assays herein described generally have a lower limit of detection (LOD) of about 1 ng/mL for α-AMA, about 5 ng/mL for β-AMA, and 1 ng/mL for γ-AMA. Because of the high affinity demonstrated by the mAbs of the present disclosure, the dynamic range of detection can be optimized depending on the application as determined by a skilled artisan.

The mAbs disclosed herein can be utilized in any immunoassay system known in the art including, but not limited to: radioimmunoassays, enzyme-linked immunosorbent assay (ELISA), "sandwich" assays, precipitin reactions, gel diffusion immunodiffusion assays, agglutination assays, fluorescent immunoassays, protein A immunoassays, immunohistochemistry assays, and immunoelectrophoresis. Such assays can be used to detect the presence and/or amounts (levels) of α-AMA, β-AMA, and γ-AMA in a biological or environmental sample. Non-limiting examples of biological samples include blood, serum, plasma, urine, spinal fluids, other body fluids or tissue samples. Environmental samples can include, but are not limited to, fungal extracts. Antibodies of the present disclosure can be bound to a solid support in which the immunoassay is to be performed. The solid support can be glass or a polymer, including, but not limited to cellulose, polyacrylamide, nylon, polystyrene, polyvinylchloride or polypropylene. The solid supports can be in the form of tubes, beads, discs microplates, or any other surfaces suitable for conducting an immunoassay.

A specific immunoassay provided herein is the use of ELISA to detect or capture an amanitin from a sample where the sample has undergone minimal preparation or modification using either one of disclosed mAb or any combination of the mAbs with or without a polyclonal antibody. The particular conditions for the ELISA will be determined by one of ordinary skill in the art. In embodiments, one or more of the mAb herein disclosed is used for a diagnostic screening to test and confirm the presence of an amanitin in a sample, such as urine or mushroom extract.

Antibodies, or fragments thereof, may be labeled using any of a variety of labels and methods of labeling known to those of skill in the art. Examples of types of labels which can be used in the present invention include, but are not limited to, enzyme labels, radioisotopic labels, non-radioactive isotopic labels, chromogenic labels, fluorescent labels, and chemiluminescent labels (see e.g., Harlow and Lane, Antibodies: A Laboratory Manual [Cold Spring Harbor Laboratory, New York 1988] 555-612).

In further embodiments, methods for detecting amanitins in a sample includes contacting the sample with an antibody by binding to a capture antibody which is then detected with a detector antibody. The detector antibody can be directly labeled with enzymes, fluorophores, etc. and thus is directly detected. The detector antibody in the present assay can be labeled using any label known in the art.

An additional embodiment provided herein is a competitive ELISA, wherein the antigen is bound to the solid support and two solutions containing the antigen from a sample and a monoclonal antibody of the present invention compete for binding of the bound antigen. The amount of monoclonal antibody bound is then measured, and a determination is made whether the sample contains an amanitin (e.g., α-AMA, β-AMA, and γ-AMA) wherein detection of mAb bound to the coated antigen indicates a small to no amanitin presence in the sample.

In an antigen capture assay, the antibody is attached to a solid support, and labeled antigen is allowed to bind. The unbound antigens are removed by washing, and the assay is quantitated by measuring the amount of antigen that is bound. In a two-antibody sandwich assay, one antibody is bound to a solid support, and the antigen is allowed to bind to this first antibody. The assay is quantitated by measuring the amount of a labeled second antibody that can bind to the antigen. These immunoassays typically rely on labeled antigens, antibodies, or secondary reagents for detection. These proteins can be labeled with radioactive compounds, enzymes, biotin, fluorochromes, other labels known in the art, and the like.

Further provided are methods and compositions to purify one or more amanitins from a sample, such as a mushroom extract utilizing the mAbs disclosed herein. A non-limiting example of such a purification method is the use of immunoaffinity chromatography in which the stationary phase comprises at least one of the mAbs described (or a functional portion thereof). The selective and strong binding of the disclosed mAbs for their target antigens makes them useful for such approaches. Such chromatographic methods are well known in the art, and the skilled artisan can utilize any such approach with the mAbs disclosed herein.

Antibody Labels

Any label known in the art can be utilized in the methods and compositions provided herein to detect mAb binding. Exemplary and non-limiting examples are provided. Visually-detectable labels are preferred over radioactive labels. Labels such as nanoparticles (gold, latex, nanobeads) or enzyme-conjugated labels are particularly useful when radioactivity must be avoided or when quick results are needed. Fluorochromes, although requiring expensive equipment for their use, provide a very sensitive method of detection. Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al., 1976 (Clin. Chim. Acta 70:1-31), Schurs, A. H. W. M., et al. 1977 (Clin. Chim Acta 81:1-40), Bobrovnik, S. A. 2003 (J. Biochem. Biochys. Methods 57:213-236), and Friguet et al 1985 (J. Immunol. Methods 77:305-319).

Examples of suitable enzyme labels include malate hydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholine esterase, etc. Examples of suitable radioisotopic labels include $^{3}H$, $^{125}I$, $^{131}I$, $^{32}P$, $^{35}S$, $^{14}C$, $^{51}Cr$, $^{57}To$, $^{58}Co$, $^{59}Fe$, $^{75}Se$, $^{152}Eu$, $^{90}Y$, $^{67}Cu$, $^{217}Ci$, $^{211}At$, $^{212}Pb$, $^{47}Sc$, $^{109}Pd$, etc. Examples of suitable fluorescent labels include a $^{152}Eu$ label, a fluorescein label, an isothiocyanate label, a rhodamine label, a phycoerythrin label, a phycocyanin label, an allophycocyanin label, an o-phthaldehyde label, a fluorescamine label, etc. Examples of chemiluminescent substrates include a luminal substrate, an isoluminal substrate, an aromatic acridinium ester substrate, an imidazole substrate, an acridinium salt substrate, an oxalate ester label, a luciferin substrate, a luciferase label, an aequorin label, etc.

Lateral Flow Immunoassays and Devices

The present disclosure provided lateral flow chromatography assay devices and methodologies utilizing mAbs to detect amanitins in a sample. Generally, such devices have an extended base layer on which a differentiation can be made between a sample application region and an evaluation region. Typically, the sample (or portion thereof) to be tested is applied to an application region, flows along a liquid transport path (e.g., nitrocellulose or wicking paper), and into an immunocomplex-formation region. A capture reagent (e.g., mAb) is present in the immunocomplex-formation region which captures the antigen to be detected (if present in the sample) and the captured antigen can be detected. For example, the assay may produce a visual signal, such as color change, fluorescence, luminescence, and the like, when indicating the presence or absence of an analyte in a biological sample. In some instances, where the device is electronic, the formation of the antigen-antibody complex creates a signal which is transformed to a visual signal, such as on a display screen.

Such devices preferably provide a clear signal indicating to a user when the antigen of interest (e.g., an amanitin) is present in the tested sample and a different signal when the antigen is absent. Non-limiting examples include a plus signal when the antigen is present and a minus signal when absent, two bands when absent and one band when present, two bands when present and one band when absent, and the like. Devices of this kind are well known in the art (e.g., pregnancy tests, ovulation tests, urine tests, spinal fluid tests, blood tests, etc.). They are used by skilled clinicians and lay person alike. Thus, there is a strong impetus to provide devices that are simple and reliable. Desirably, the assays are single-step devices wherein the user need only apply the sample prior to viewing the result.

Kits

The present disclosure also provides kits which are useful for carrying out detection methods of the present invention. The kit includes a container comprising a monoclonal antibody produced by at least one hybridoma cell line of the present invention and instructions for using the monoclonal antibody for the purpose of binding to the amanitins to form an immunological complex such that the presence or absence of the immunological complex correlates with or indicates the presence or absence of the amanitins in the sample. The kits can comprise a first container means containing the antibodies described herein. The kit can also comprise other container means having solutions necessary or convenient for carrying out the invention. The container means can be made of glass, plastic, foil, the like, and combinations thereof and can be any suitable vial, bottle, pouch, tube, bag, box, etc. The kit can also contain written information, such as procedures for carrying out the present invention or analytical information, such as the amount of reagent contained in the first container means. The container means can be in another container means (e.g., a box, bag, etc.) along with the written information.

Having generally described this invention, the same will be better understood by reference to certain specific examples, which are included herein to further illustrate the invention and are not intended to limit the scope of the invention as defined by the claims.

EXAMPLES

Example 1

Hybridoma and Monoclonal Antibody Production

The Institutional Animal Care and Use Committee of the United States Department of Agriculture, Western Regional Research Center approved the experimental procedures used in these studies (protocol #16-1). Three 6-week-old female BALB/c mice were immunized by intraperitoneal injection (i.p.) of 100 μL of a 1:1 Sigma Adjuvant System (Sigma-Aldrich, St. Louis, Mo.) containing 50 μg of an 8-amino-acid fragment from α-AMA conjugated through a dihydroxy-isoleucine to KLH ("PERI-AMA-KLH") (Bever et al, (2018)). Two subsequent booster immunizations were administered i.p. at 2-week intervals using 20 μg of PERI-AMA-KLH in Sigma Adjuvant System. Serum were collected one week after the third immunization. Another two booster immunizations were performed four months later, 2-weeks apart, and serum was collected one week after this round of immunizations. After determining by indirect ELISA that the antibody response was still elevated to this target immunogen, a final booster immunization containing 10 μg of PERI-AMA-KLH in saline was administered i.p. four days prior to being euthanized and cell fusion.

For serum antibody screening, black 96-well microtiter plates (Nunc, Thermo Fisher Scientific, Waltham, Mass.) were coated at 1 μg/mL with PERI-AMA-BSA (the same 8-amino-acid fragment of α-AMA conjugated through a dihydroxy-isoleucine to bovine serum albumin (BSA)) for 1 hour at 37° C. in carbonate buffer (0.05 M carbonate-bicarbonate, pH 9.6). Then, the plates were blocked with 3% non-fat dry milk in tris-buffered saline with 0.05% Tween-20 (TBST). Serum was loaded at a dilution of 1:100 in TBST and serially diluted. After incubation for 1 hour, plates were washed three times with TBST. Plates were then loaded with horse radish peroxidase labeled goat-anti-mouse (Sigma) at 1:5000 in TBST. After incubation and washing, the plates were loaded with SUPERSIGNAL West Pico Chemiluminescent substrate (Fisher), incubated for 3 minutes and then luminescent counts were recorded on a VICTOR MULTI-LABEL COUNTER (PerkinElmer, Waltham, Mass.).

The cell fusion and expansion procedures were completed as previously described (Stanker et al, J. Immunol. Meth., (2008) 336:1-8). Screening of the cell culture plates following cell fusion, in particular the use of an indirect competitive inhibition assay, was carried out as previously described with minor modifications (Spier et al, Analyt. Biochem., (2009) 387:287-93). Wells of clear-bottom microtiter plates coated with PERI-AMA-BSA were pre-loaded with 50 μL/well of either TBST for noncompetitive screening or α-AMA at 500 ng/mL for competitive screening. Antibody activity was visualized using Enhanced K-BLUE Substrate (Neogen, Lexington, Ky.) and read on a VERSAMAX Microplate Reader (Molecular Devices, San Jose, Calif.).

Hybridomas from wells exhibiting significant reaction to the presence of α-AMA (reduction of activity) were selected for clonal expansion. Cells were cloned by limiting dilution, repeated until every well with cell growth presented positive activity via ELISA. MAbs were purified from cell culture supernatant on a Protein G Sepharose affinity column (GE Healthcare Life Sciences, Pittsburgh, Pa.), eluted with 0.1 M glycine-HCl, pH 2.7. Purified protein was extensively dialyzed against PBS and then stored at −20° C. until further use.

Antibody protein concentrations were determined on a NANODROP Lite Spectrophotometer (Thermo). Antibody isotyping was completed using an ISOSTRIP Mouse Monoclonal Antibody Isotyping Kit (Roche, Indianapolis, Ind. USA), following the manufacturer's protocol. Purified mAbs were titrated by indirect ELISA to determine the concentration of antibody at half of the maximal signal. This determined concentration was used as the working concentration of antibody for the cELISAs to evaluate antibody cross-reactivity.

Unlike early reports of generating amanitin-conjugated immunogens that exhibit toxicity (Cessi and Fiume, Toxicon, (1969) 6:309-10), this immunogen did not cause any death in both mice or rabbits, corroborating the low toxicity observed by other investigators (Andres and Frei, Toxicon, (1987) 25:915-22). Following the screening of the fusion plates, there were 16 positive cultures (OD>0.7) of which 4 cultures exhibited substantial inhibition (OD decreased by 0.5 or greater) in the presence of α-AMA in cELISA. Only 2 of these grew stably and were cloned multiple times until every well of the cell culture plate with cell growth elicited a positive indirect ELISA response to PERI-AMA-BSA. The resulting mAbs were designated "9G3.2" or "AMA9G3" (produced by hybridoma PTA-125922) and "9C12.2" or "AMA9C12" (produced by hybridoma PTA-125923). Both mAbs are isotype $IgG_1$ possessing kappa light chains.

Example 2

Monoclonal Antibody Characterization

Indirect cELISAs were completed using a panel of inhibitors to determine the selectivity of the mAbs. The cELISA procedure was nearly the same as that described above for the serum screening, except for the addition of inhibitors mixed with antibody during the primary antibody incubation step. The inhibitors tested were α-AMA (≥90%, Enzo Life Sciences, Farmingdale, N.Y.), β-AMA (≥90%, Enzo), γ-AMA (≥90%, Enzo), microcystin-LR (≥95%, Enzo), nodularin (≥95%, Enzo), phalloidin (>90%, Enzo), phallacidin (≥85%, Sigma), pysilocybin (>99%, Cerilliant, Round Rock, Tex.), muscimol (>99%, Abcam, Cambridge, Mass.), ibotenic acid (>98%, Abcam). Each analyte stock was dissolved in $dH_2O$, then serially diluted into TBST starting at the highest concentration of 1,000 ng/mL and assessed in triplicate. Data were analyzed using a 4-parameter logistic equation (GRAPHPAD PRISM 7 Software, La Jolla, Calif.) to determine the concentration of inhibition at half of the maximal signal ($IC_{50}$). Cross-reactivity (%) was calculated as follows: ($IC_{50}$ α-AMA)/($IC_{50}$ test inhibitor)×100.

All kinetic measurement experiments on the mAbs were performed on a KinExA 3200 with Autosampler (Sapidyne Instruments, Boise, Id.) and data were analyzed using KinExA Pro software provided by Sapidyne. Affinity values ($K_d$) utilized their template protocol for an Equilibrium Experiment and kinetic parameters were determined using the Kinetics Injection method. Flow rates and volumes used the default settings defined in the software.

Polymethylmethacrylate (PMMA) particles (aliquots of 200 mg, Syringa Labs, Boise, Id.) were adsorption coated with 30 μg of BSA-AMA-PERI in 1 mL of carbonate buffer for 1 hour at room temperature with end-over-end rotation. The particles were blocked with a solution of 1% BSA (Sigma) in phosphate buffered saline for 1 hour at room temperature with end-over-end rotation and stored at 4° C. for no more than one week before use. The diluent for all reagents was PBS containing 1% BSA. Three antibodies were evaluated, two mouse mAbs (9G3.2 (produced by hybridoma PTA-125922) and 9C12.2 (produced by hybridoma PTA-125923) generated from this study) and one rabbit polyclonal antibody #58 generated from the previous study (Bever et al, (2018)). The secondary antibody used for the mouse antibody experiments was DyLight650 labeled anti-mouse Ig (Fisher) (used at 0.5 μg/mL) and the secondary antibody used for the rabbit antibody experiments was AlexaFluor647 labeled anti-rabbit Ig (Jackson Immunoresearch, West Grove, Pa.) (used at 0.25 μg/mL).

Signal test runs were completed on each antibody to determine the amount of antibody needed to generate the appropriate signal change (1Δv). Then, for the equilibrium experiments, antibody was prepared at 2× this concentration and then mixed with an equal volume of a solution containing α-AMA diluted 2-fold, ranging from 300 ng/mL (326 nM) to 9.2 pg/mL (10 pM) final concentrations, including one sample with no α-AMA and one sample containing only diluent (NSB, non-specific binding). For the kinetics injection experiments, the same 2× antibody concentration was used, along with solutions containing α-AMA diluted 2-fold, ranging from 920 ng/mL (1000 nM) to 1.8 ng/mL (2 nM). The equilibrium and kinetics injection experiments were completed in duplicate.

In order to determine the specificity and sensitivity of the monoclonal antibodies, and thus how effective they would be for selectively detecting amatoxins, a panel of cyclic peptides and smaller chemicals were tested. These included the bicyclic heptapeptides known as phallotoxins (phalloidin and phallacidin) also produced by *A. phalloides*, chemical toxins (psilocybin, muscimol, and ibotenic acid) produced by other mushrooms, and cyclic peptides (nodularin and microcystin-LR) produced by cyanobacteria. Of these analytes tested, mAb 9G3.2 (produced by hybridoma PTA-125922) was competitively inhibited by all of the amatoxins, α-AMA, β-AMA, and γ-AMA, while mAb 9C12.2 (produced by hybridoma PTA-125923) was only competitively inhibited by α-AMA and γ-AMA (Table 1, FIG. 1A, and FIG. 1B). Neither mAb bound to any of the other compounds tested.

TABLE 1

Cross-reactivity (%) of mAbs with various compounds.

| | mAb 9G3.2 | | mAb 9C12.2 | |
|---|---|---|---|---|
| Toxin | $IC_{50}$ (ng/mL) | Cross reactivity (%) | $IC_{50}$ (ng/mL) | Cross reactivity (%) |
| α-amanitin | 1.57 ± 0.07 | 100 | 2.66 ± 0.18 | 100 |
| β-amanitin | 24.2 ± 6.2 | 6.5 | >1000 | <0.3 |
| γ-amanitin | 1.63 ± 0.21 | 96 | 2.3 ± 0.31 | 115 |
| phalloidin | >1000 | <0.3 | >1000 | <0.3 |
| phallacidin | >1000 | <0.3 | >1000 | <0.3 |
| psilocybin | >1000 | <0.3 | >1000 | <0.3 |
| microcystin-LR | >1000 | <0.3 | >1000 | <0.3 |
| nodularin | >1000 | <0.3 | >1000 | <0.3 |
| ibotenic acid | >1000 | <0.3 | >1000 | <0.3 |
| muscimol | >1000 | <0.3 | >1000 | <0.3 |

Figure 1B:
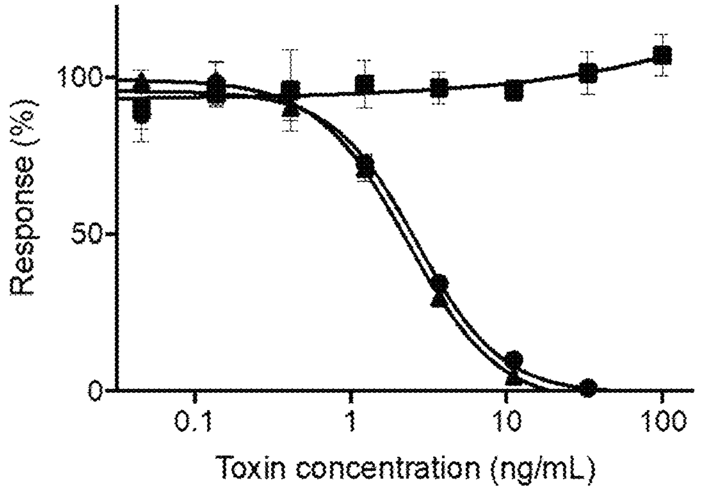

The standard curves for both mAbs against α-AMA, β-AMA, and γ-AMA toxins are shown in FIG. 1A and FIG. 1B. There is no reduction in signal response for mAb 9C12.2 (produced by hybridoma PTA-125923) when tested against different concentrations of β-AMA (FIG. 1B), whereas for mAb 9G3.2 (produced by hybridoma PTA-125922) all three of the toxins do competitively inhibit at higher concentrations (FIG. 1A). The steep slope generated by competitive inhibition from α-AMA and γ-AMA was also seen in the previous work with the rabbit pAb #58 (Bever et al, supra). The curves for the two mAbs indicate that both are good candidates for components of qualitative assays for α-AMA and γ-AMA and that mAb 9G3.2 may also be a good candidate for a quantitative assay for β-AMA.

While both mAbs exhibited competitive inhibition from α-AMA and γ-AMA, mAb 9G3.2 exhibited slightly higher sensitivity with an $IC_{50}$ of 1.57 ng/mL for α-AMA (Table 1 FIG. 1A). Previously described mAbs to amatoxins report an $IC_{50}$ of 66 ng/mL for α-AMA (He et al, supra). A conservative estimate for the limit of detection (LOD) for α-AMA or γ-AMA with the mAb 9G3.2 assay is 1 ng/mL, accounting for the large (30%) variation in signal at low to no concentrations of toxin. Because of the propensity for samples (mushroom extracts) to contain all three amatoxins, mAb 9G3.2 was selected for use in the cELISAs for the extraction studies.

For the two mAbs from this study and one rabbit pAb from previous work (Bever et al, supra), a final concentration of 10 nM was used for both equilibrium and kinetics injection studies. Table 2 shows the affinity ($K_d$) and kinetic parameters ($k_{on}$ and $k_{off}$) values obtained for each antibody tested against α-AMA as the free ligand (in Table 2, $K_d$=equilibrium dissociation constants, $k_{on}$=association rate constants, $k_{off}$=dissociation rate constants. $k_{off}$ was calculated as $K_d \times k_{on}$). Antibodies with these kinetic parameters are considered to have very high affinity, which can impact the amount needed in a detection device or purification column to achieve the end goal (Ag-binding).

TABLE 2

Affinities ($K_d$) and kinetic parameters ($k_{on}$ and $k_{off}$) for antibodies binding to α-amanitin measured by KinExA.

| Antibody | $K_d$ (M) | $k_{on}$ ($M^{-1}$ $s^{-1}$) | $k_{off}$ ($s^{-1}$) |
|---|---|---|---|
| rab pAb #58 | $3.5 \times 10^{-11}$ | $4.1 \times 10^{6}$ | $1.4 \times 10^{-4}$ |
| mAb 9G3.2 | $6.4 \times 10^{-11}$ | $4.7 \times 10^{7}$ | $3.0 \times 10^{-3}$ |
| mAb 9C12.2 | $9.3 \times 10^{-10}$ | $1.7 \times 10^{7}$ | $1.4 \times 10^{-2}$ |

Example 3

Mushroom Extraction

Whole mushroom specimens were identified, dried, and provided as a generous gift from Ms. Adams and Dr. Bruns (University of California, Berkeley). The specimens included two that were known to contain amatoxins, *A. phalloides* and *A. ocreata*, and one that was known to not contain amatoxins, but from the same genus, *A. gemmata*. Small portions of the specimens were weighed (~100-200 mg) and then placed into a 15 mL Falcon tube containing one of the five extraction buffers: 1) methanol (methanol: water:0.01N HCl, 5:4:4, v:v:v), 2) $diH_2O$, 3) phosphate buffer (PB; 0.1 M, pH 7.6), 4) PB with Tween-20 (PBT), or 4) TBST at the ratio of 1 mL per 0.1 mg tissue. The samples that were extracted with the methanol buffer were shaken for 1 hour at room temp and then centrifuged at 1000×g for 10 mins. Aliquots of the supernatant were drawn off, diluted in TBST as necessary, and assessed by indirect cELISA. The samples in $diH_2O$, PB, PBT, or TBST were briefly shaken by hand for 1 min and then immediately an aliquot of the liquid phase was drawn off, diluted in TBST as necessary, and assessed by indirect cELISA. At least two individual mushrooms from each species were extracted, and extractions for each extraction condition were completed in duplicate.

Figure 2A:
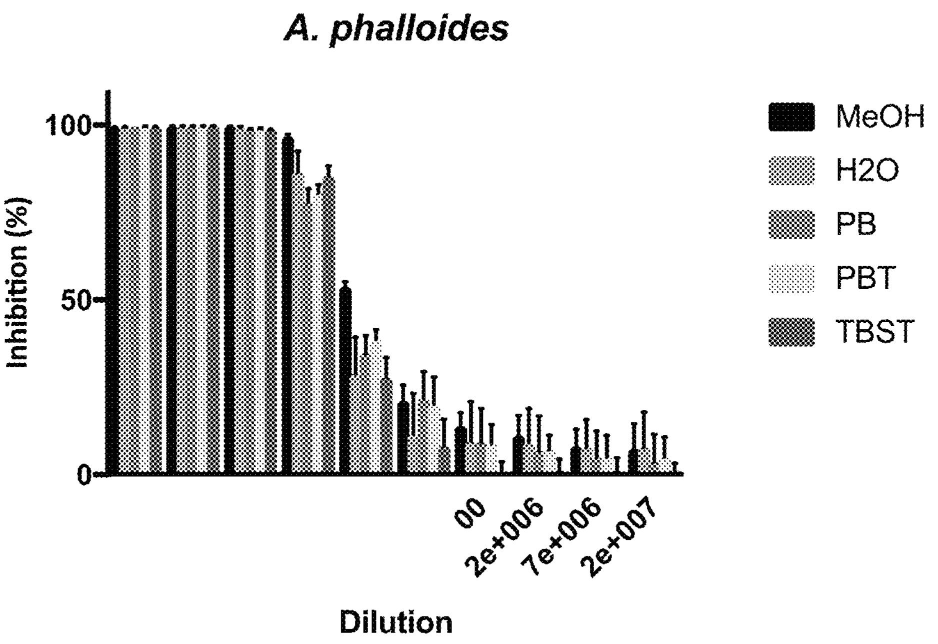
FIG. 2A, FIG. 2B and FIG. 2C provide representative cELISA inhibition profiles illustrating the amount of inhibition from the tested extraction conditions at varying dilutions of mushroom extracts obtained from *Amanita phalloides* (FIG. 2A), *A. ocreata* (FIG. 2B), and *A. gemmata* (FIG. 2C). The extraction conditions were as follows: 1) MeOH:methanol:water:HCl for 1 hour; 2) $H_2O$:di$H_2O$, 1 minute, 3) PB: phosphate buffer, 1 minute, 4) PBT: PB with Tween-20, 1 minutes, and 5) tris-buffered saline with Tween-20, 1 minute.
Figure 2B:
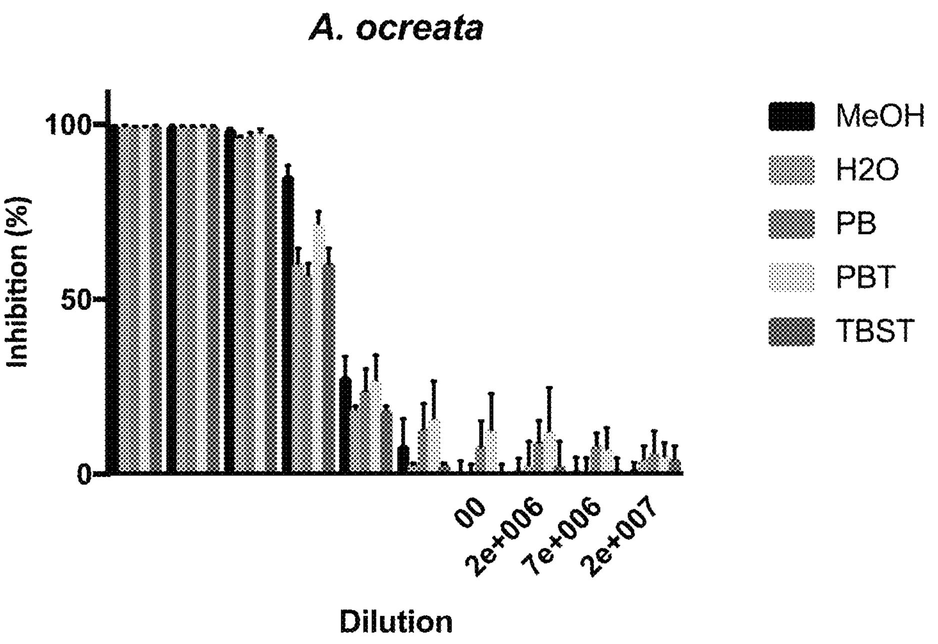

For the purposes of exploring the feasibility of performing extractions on-site and quickly, five different extraction solutions were tested. The commonly employed extraction using methanol and dilute acid was compared to extractions with more innocuous reagents such as phosphates, tris, and Tween-20. The extraction solutions were tested on three different mushroom species (two known to contain amatoxins and one known to not contain amatoxins). For both species known to contain amatoxins (*A. phalloides* and *A. ocreata*), the toxin was extractable with all tested extraction conditions, indicated by the 100% inhibition when tested using the 9G3.2 anti-AMA cELISA at dilutions up to and including a nearly 10,000-fold dilution of the extract (FIG. 2A and FIG. 2B). With increasing dilutions, it is expected that the amount of inhibition would decrease, with a conservative estimate of background being up to 30%. The slight difference in the amount of inhibition observed between the methanol buffer compared to the four aqueous extraction buffers at the 27,000-fold and 81,000-fold dilutions for *A. phalloides* and the 27,000-fold dilution for *A. ocreata* suggest that the faster, aqueous extraction conditions might not extract the amatoxins as efficiently. Nonetheless, for a qualitative, rapid test, using these aqueous rapid extraction methods are highly suitable for the determination of amatoxins from mushroom samples when the extract is diluted less than approximately 30,000-fold.

Using simple, aqueous solutions prepared in such a short time is unique. Previous methods use methanol and acid for extraction, or another organic solvent. This approach reduces the time needed for extraction from 24 hours to a minimum of about one minute. Overall, these results suggest that these quick aqueous-based extraction methods are highly suitable for this purpose of rapid detection, but if improved extraction efficiency were desired, pooling consecutive extracts, increasing time, and adding co-solvents independently are worthwhile approaches.

One aspect of the toxin extraction procedure that could be avoided is the need for sample maceration, which increases protection of the researcher from potential dust exposure. In our previous work and that of many others, the mushroom tissue is ground to a powder (Enjalbert et al, (1999), supra; Sgambelluri et al, supra; Hu et al, supra; Garcia et al, supra; McKnight et al, supra; Bever et al, supra; Stijve & Seeger, Z. Naturforsch., (1979) 34:1133-38). In this study, however, we did not grind the samples and still achieved sufficient toxin extraction suitable for cELISA detection.

Amatoxin concentrations have been reported to vary within *Amanita* species (e.g., *A. exitalis, A. verna, A. bisporigera, A. virosa*, etc.) (Enjalbert et al, J. Toxicol. Clin. Toxic, (2002) 40:715-57; Seeger & Stijve, Z. Naturforsch., (1979) 34:3330-3; Zhou et al, Mycoscience, (2017) 58:267-73), as well as those in other genera (i.e., *Lepiota* and *Galerina*)(Sgambelluri et al, supra; Enjalbert et al, Mycologia, (2004) 96:720-9) such that the α-AMA concentration could be as much as one-log (10-fold) different (higher or lower) than found in *A. phalloides* (Sgambelluri et al, supra). Concentrations of amatoxins can also vary depending on developmental stage (Hu et al, supra) or location (Enjalbert et al, (1999), supra; Zhou et al, supra). However, these variations are relatively negligible in this assay given the ability to detect toxin in a 4-log-fold (10,000-fold) dilution of the extract.

Figure 2C:
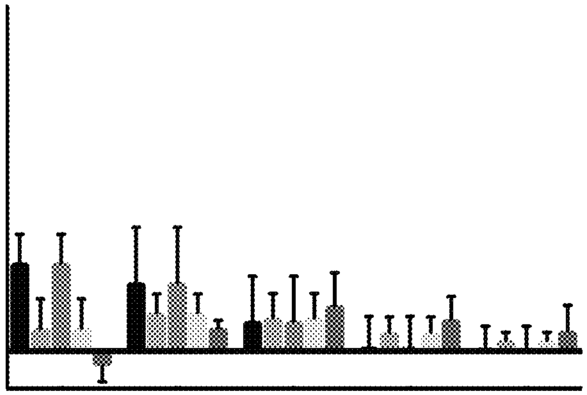

Matrix effects (variations exceeding 30% inhibition) at the 1- and 3-fold dilutions for the methanol and PB buffers of the non-toxin containing mushroom *A. gemmata* were evident, albeit minor (FIG. 2C). A simple 9-fold or greater dilution of the extract, or completing the extraction at a higher ratio than 1 mL of buffer to 0.1 mg of tissue, would overcome this issue. Furthermore, given the large concentration of amatoxins in deadly mushroom species, obtaining a potentially false-positive mushroom extract at a 10-fold or lower dilution would probably require a person to consume at least 1,000 or more of these mushrooms to obtain the same lethal concentration of amatoxins in one deadly mushroom.

Example 4

Lateral Flow Device

The feasibility of formatting the antibody and the antigen for amatoxin into a lateral flow device has been demonstrated. Two haptens (PERI-AMA-KLH and LB (an NHS-activated-α-AMA hapten purchased from Levena Biopharma, San Diego, Calif.)) conjugated to BSA were used as test line coating antigens. mAb AMA9G3 was conjugated to 40 nm gold particles using a Colloidal Gold Conjugation Kit according to manufacturer's instructions (DCN, San Diego, Calif.) to generate a visual band when reaction with the coated (test and control) lines occurred. The conjugation of mAb AMA9G3 to gold nanoparticles can be completed with achieved stability at a range of coating conditions, indicating a broad range of acceptable pHs and mass loading conditions, thus allowing the assay to be highly tunable. The format of this assay was a competitive assay, wherein the line disappears when the toxin is present at detectable levels. When testing either hapten as the test line, complete inhibition of the signal was observed at 10 ng/mL of alpha-amanitin and gamma-amanitin, independently, and the limit of detection was observed around 1 ng/mL of alpha-amanitin and gamma-amanitin, independently. The LOD for beta-amanitin was slightly higher around 30 ng/mL. Cross-reactivity with other near neighbor compounds was tested and the test strips did not detect psilocybin, muscimol, and ibotenic acid, nor for cyclic peptides microcystin-LR or nodularin. The test strips did detect phallotoxins (phalloidin and phallacidin) at 200 m/mL (CR 0.005%). The optimized assembled test strips were tested with urine samples (≥50 human specimens, 38 dogs and 1 cat), with no apparent urine components that interfered with detection.

Figure 3:
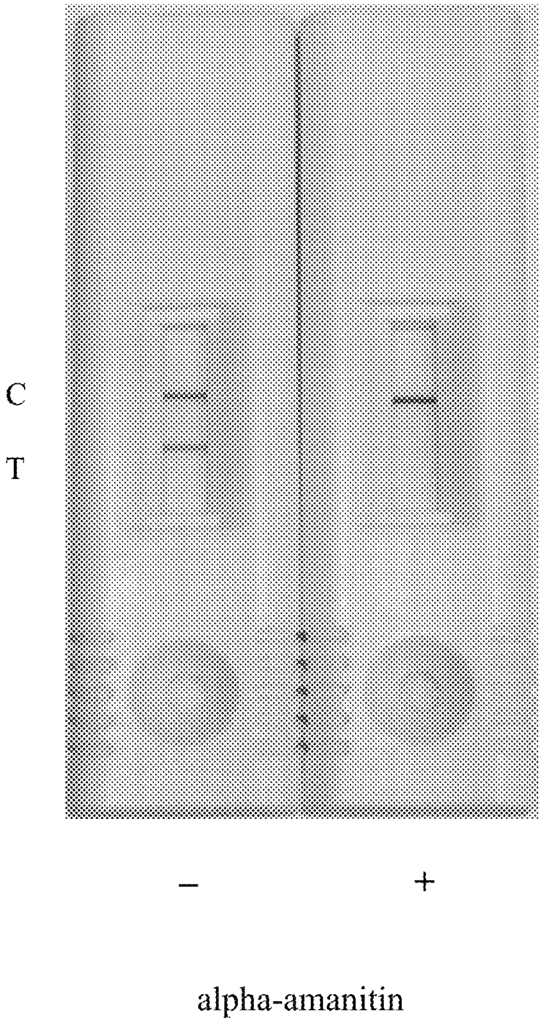
FIG. 3 provides a picture of a lateral flow test strip assay using mAb 9G3.2 in a competitive assay where the absence of a band on the “T” line indicates the presence of amanitin in a sample. Positive and negative results are shown. “C” indicates the control line and “T” indicates the test line.

Mushroom extracts, using our newly identified and simplified extraction method, were tested for presence of amatoxins from wild mushrooms. To date, 96 different mushroom species have been tested and all of them have produced accurate test results addressing if the mushroom is known to contain amatoxins. A few species known to contain other toxins (i.e., hallucinogenic compounds, gastrointestinal irritants) were tested and produced negative results, which is consistent with the fact that they do not contain the specific amanitin chemicals that this test is testing for. For both urine and mushroom extracts, no additional sample processing is required, and the test takes 10 minutes to run and obtain a visual result (FIG. 3).

The end goal of such detection devices is to provide rapid, point-of-care detection of amatoxin in different sample types, such as clinical samples (e.g., human urine), veterinary samples (e.g., dog urine), and mushroom extracts. For human patients with amatoxin poisoning, amatoxin levels in urine have been shown to range from 5-5,000 ng/mL (Jaeger et al, J. Toxicol. Clin. Toxicol., (1993)). These concentrations were often detected between 12-36 hours post-ingestion, and the concentration usually dropped over time. A rapid, point-of-care test would allow for testing early samples that are more likely to contain higher amounts of amatoxin. For detection, thus far we have successfully generated lateral flow immunoassay test strips using mAb 9G3.2 and can detect amatoxins down to 1 ng/mL in human urine (unprocessed, non-extracted, non-neutralized) spiked with known amounts of amatoxins, and from mushrooms extracted with solutions as simple as salt water. A variety of mushrooms, including all known to contain amatoxin appeared positive and those known to not contain amatoxins were negative. Thus, these test strips could be used for human diagnostics, veterinary diagnostics, and for personal use testing mushrooms. In a clinical setting, the same test strip for urine could be used to test any mushroom material a patient (dog or human) might have salvaged even if it is now unidentifiable to a mycologist.

Example 5

Amanitin Purification

The amanitins are difficult to synthesize in the laboratory. Both α-AMA and β-AMA, are used as chemical standards and purified α-AMA is used for cancer therapeutics in the development of antibody-drug (α-AMA) conjugates (ACDs). α-AMA is isolated by column extraction and elution using either mAb disclosed herein. β-AMA is isolated by absorbing α-AMA onto a column coated with mAb 9C12.2 and allowing the β-AMA to flow through the column. Alternately, both α-AMA and β-AMA are isolated by first absorbing and eluting these two amanitins, followed by re-absorbing the eluate on a column coated with mAb 9C12.2 to collect only β-AMA as a flow-through.

To this end, we have conjugated a sepharose column with mAb 9G3.2 according to established protocols (Maurer et al, J. Chromatog B, (2000) 748:125-35). A standard of alpha-AMA and allowed it to bind the antibody. We were then able to wash the column, and then elute the standard in an organic elution buffer. These elutes were assessed by thin-layer chromatography and the fractions containing the toxin were identified. The column has been reused as few times, and possibly many more times than we have tested so far.

Urine samples containing amatoxins have also been subjected to clean-up by immunoaffinity purification. In these low-level samples, the column was able to concentrate the amatoxins, as well as permit washing of the target analyte thus reducing the presence of other compounds in the matrix. These eluates have been suitable for detection by LC-MS/MS.

While the invention has been described with reference to details of the illustrated embodiments, these details are not intended to limit the scope of the invention as defined in the appended claims. The embodiment of the invention in which exclusive property or privilege is claimed is defined as follows:

What is claimed is:

1. A monoclonal antibody produced by a hybridoma cell line of deposit accession number PTA-125922 or PTA-125923.

2. The monoclonal antibody of claim 1, wherein the antibody is isolated and purified.

3. A composition comprising the monoclonal antibody of claim 1.

4. The composition of claim 3, further comprising a label selected from the group consisting of: enzyme labels, radioisotopic labels, non-radioactive isotopic labels, chromogenic labels, fluorescent labels, chemiluminescent labels, and combinations thereof.

5. A hybridoma cell line which produces the monoclonal antibody of claim 1, wherein the cell line has deposit accession number PTA-125922 or PTA-125923.

6. A method for detecting alpha-amanitin, beta-amanitin, or gamma-amanitin in a sample, comprising: (i) incubating a sample with a monoclonal antibody of claim 1; and (ii) detecting an immunological complex comprising the monoclonal antibody and the alpha-amanitin, beta-amanitin, or gamma-amanitin, wherein the presence or absence of the immunological complex indicates the presence or absence of the alpha-amanitin, beta-amanitin, or gamma-amanitin in the sample.

7. The method of claim 6, wherein the sample is a human sample or an animal sample.

8. The method of claim 7, wherein the sample is a urine sample.

9. The method of claim 6, wherein the sample is a mushroom extract sample.

10. The method of claim 9, wherein the mushroom extract sample does not contain an organic solvent.

11. The method of claim 6, further comprising the step of isolating the immunological complex formed between the monoclonal antibody and the alpha-amanitin, beta-amanitin, or gamma amanitin.

12. A kit for detecting alpha-amanitin, beta-amanitin, or gamma-amanitin in a sample, comprising: (1) a container comprising a monoclonal antibody produced by a hybridoma cell line of deposit accession number PTA-125922, PTA-125923, or mixtures thereof; and (2) instructions for using the antibody for the purpose of binding to alpha-amanitin, beta-amanitin, or gamma-amanitin to form an immunological complex and detecting the formation of the immunological complex such that presence or absence of immunological complex correlates with presence or absence of alpha-amanitin, beta-amanitin, or gamma-amanitin in said sample.

13. A lateral flow device, comprising a monoclonal antibody produced by a hybridoma cell line of deposit accession number PTA-125922, PTA-125923, or mixtures thereof.

14. A method for purifying an amanitin from a sample, comprising: (i) incubating a sample comprising the amanitin with a monoclonal antibody of claim 1 under conditions where an immunological complex comprising the monoclonal antibody and the amanitin is formed; (ii) isolating the immunological complex from the sample; (iii) decoupling the immunological complex resulting in the release of the amanitin from the monoclonal antibody; and (iv) separating the amanitin from the monoclonal antibody, thereby purifying the amanitin.

15. The method of claim 14, wherein the amanitin is alpha-amanitin, beta-amanitin, or gamma-amanitin and the monoclonal antibody is produced by a hybridoma cell line of deposit accession number PTA-125922 (mAb 9G3.2).

16. The method of claim 14, wherein the amanitin is alpha-amanitin, or gamma-amanitin and the monoclonal antibody is produced by a hybridoma cell line of deposit accession number PTA-125923 (mAb 9C12.2).

* * * * *